United States Patent [19]

Carlier et al.

[11] 4,430,332
[45] Feb. 7, 1984

[54] ETHERS OF 1-(2-PROPYNYLOXY)-2-AMINO-3-PROPANOL

[75] Inventors: Patrick Carlier; André J. C. Monteil, both of Chatel-Guyon; Jacques A. L. Simond, Chamalieres, all of France

[73] Assignee: Centre Europeen de Recherches Mauvernay, Riom, France

[21] Appl. No.: 218,176

[22] Filed: Dec. 19, 1980

[30] Foreign Application Priority Data

Dec. 28, 1979 [FR] France ................. 7932008

[51] Int. Cl.³ .................. A61K 31/535; A61K 31/40; C07D 295/08; C07D 207/04
[52] U.S. Cl. ............................ 424/248.57; 544/170; 544/174; 548/574; 548/575; 424/274
[58] Field of Search ................. 260/326.5 R; 544/170, 544/174; 424/274, 248.57; 548/575, 574

[56] References Cited

U.S. PATENT DOCUMENTS

Re. 30,577  4/1981  Busch et al. ................ 548/574
3,884,923   5/1975  Mauvernay et al. .......... 424/250
4,060,613  11/1977  Ferland et al. .............. 424/250

Primary Examiner—Paul M. Coughlan, Jr.
Assistant Examiner—D. B. Springer
Attorney, Agent, or Firm—Abelman, Frayne & Rezac

[57] ABSTRACT

The invention is dealing with compounds of the formula:

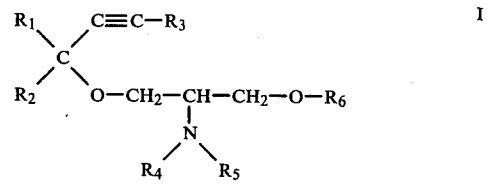

and pharmaceutically acceptable salts thereof, in which $R_1$ and $R_2$ each represent a lower alkyl radical or a phenyl radical, or, together with the carbon atom to which they are bound, a cycloalkyl radical having at the most 7 carbon atoms; $R_3$ represents hydrogen, a lower alkyl radical, or the phenyl radical; $R_4$ and $R_5$ each represent a lower alkyl radical, or, together with the nitrogen atom to which they are bound, a heterocyclic amino radical such as the pyrrolidinyl or morpholino radicals; and $R_6$ represents a lower alkyl radical, a phenyl radical, a benzyl radical, or the 1-ethynylcyclohexyl radical, which compounds can be used in the treatment of angina pectoris.

6 Claims, No Drawings

ETHERS OF 1-(2-PROPYNYLOXY)-2-AMINO-3-PROPANOL

The present invention is referring to new ethers of 1-(2-propynyloxy)-2-amino-3-propanol, to processes for their preparation and to a pharmaceutical preparation containing said ethers as the active principle.

More particularly the present invention is dealing with compounds of the general formula:

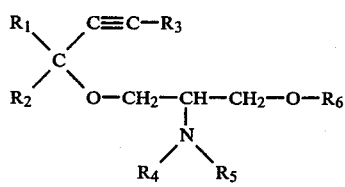

in which $R_1$ and $R_2$ each represent, independently of one another, a lower alkyl radical or a phenyl radical, or, together with the carbon atom to which they are bound, a cycloalkyl radical having at the most 7 carbon atoms; $R_3$ represents hydrogen, a lower alkyl radical or the phenyl radical; $R_4$ and $R_5$ being identical or different each represent a lower alkyl radical, or, together with the nitrogen atom to which they are bound, a heterocyclic amino radical, such as the pyrrolidinyl and morpholino radicals; $R_6$ represents a lower alkyl radical, a phenyl radical, a benzyl radical or the 1-ethynylcyclohexyl radical, as well as the pharmaceutically acceptable salts of these compounds.

The invention is further dealing with a process of obtaining the compounds I from a suitably substituted ether of 2-chloro-3-amino propanol and an acetylenic alcohol, preferably by phase-transfer catalysis.

The invention also concerns the use of the compounds I or their pharmaceutically acceptable salts in the treatment of cardiac disturbances, especially in humans.

There are already numerous known aryloxyamino propanols deriving from the structure of 1-isopropylamino-3-(1-napthyloxy)-2-propanol (propanolol), a compound known for its β-blocking properties. The modifications made to this structure concern either the naphthyl radical (by substitution and/or introduction of an other unsaturated group, or the aminopropanol chain itself (by etherification and/or isomerisation).

In certain cases, the compounds obtained retain the β-blocking activity; this is the case for example with 2,3-cis-1,2,3,4-tetrahydro-5-(2-hydroxy-3-tert.butyl-aminopropoxy)-2,3-naphthalenediol (DE No. 2.258.995).

In other cases, the expected β-blocking activity cannot be demonstrated and the compounds are active on the central nervous system; this occurs for example with 2-isopropylamino-3-(1-naphthyloxy)-1-propanol, a position isomer of propanolol [J.Med.Chem. 13, 398 (1970)]. Compounds whose general structure corresponds to ethers of the previously mentioned compound also have no β-blocking properties, but are active on the central nervous system (U.S. Pat. No. 4,060,613).

In contrast, it has now been discovered that compounds whose general structure can be considered to resemble that of the compounds described in U.S. Pat. No. 4,060,613, but in which the aminopropane chain is no longer substituted by an aryloxy radical, have interesting β-blocking properties.

These compounds, having the general formula (I), are prepared in accordance with the following reaction scheme preferably by means of phase-transfer catalysis:

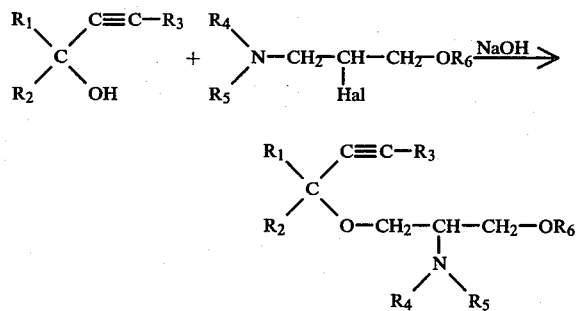

Hal means halogen and preferably chlorine. It should be noted that this reaction, which is brought about through an immonium ion, leads to a rearrangement of the amino function—$NR_4R_5$.

The halogenated derivative used in this synthesis is prepared according to known means indicated, for example, in U.S. Pat. No. 3,663,566.

The preferred reaction is effected by adding small quantities of the halogenated derivative to a solution constituted of a suitable acetylenic alcohol, an equivalent quantity or small excess of a base, preferably sodium-hydroxide, and a phase-transfer catalyst, such as benzyltriethylammoniumchloride.

If necessitated by the excessive viscosity of the reaction medium, a solvent, such as benzene or methylene chloride, is added before refluxing. The compound obtained is then extracted in the usual manner, e.g. with the aid of ether.

According to a variant of this process, the halogenated derivative can be replaced by the corresponding sulfonate, prepared by the usual means from the amino-alcohol $N(R_4R_5)$—$CH_2$—$CH(OH)$—$CH_2OR_6$ and a sulfonylhalide, such as mesylchloride or tosylchloride. This variant is to be used in preference when the substituent $R_6$ has functions which are liable to be degraded by the halogenation agents used to obtain the halogenated derivative.

The cardiovascular activity of the compounds of the invention was demonstrated in the dog, according to the following procedure.

The animal was anaesthetised with chloralose and record was kept of:
- the arterial frequency at a femoral artery via a probe connected to a BELLET AND HOWEL pressure cell,
- the amplitude of cardiac contractions (Contractile force) by means of a strain gauge fixed by four suture points on the left ventricular epicardium on the great axis of the organ, after thoracotomy at the 5th lefthand intercostal space.

The β sympathetic reactivity was also tested by recording the inhibition of tachycardia induced by an injection of isoprenaline (0.5 g kg$^{-1}$ I.V.) before administration of the tested product, and then 5 minutes after this administration, and then every 15 minutes.

Table A hereinafter consolidates the measurements carried out on these different parameters, the results being expressed as percentage of maximum variation with respect to the values before treatment. All the compounds of the invention were administered in doses of 5 mg kg$^{-1}$ I.V., with the exception of compound no. 3 which was administered in doses of 1 mg kg$^{-1}$ I.V.

TABLE A

| Compound no.* | Cardiac frequency | Arterial pressure | Contractile force | Tachycardia inhibition |
|---|---|---|---|---|
| 1 | −15% | −28,3% | +28% | −58,7% |
| 2 | −28% | −36% | −45% | −18% |
| 3 | −44% | −38% | −50% | −62% |
| 4 | −19% | 0 | −11% | −23% |
| 6 | −17,7% | −18,2% | +70,2% | −62,2% |
| 7 | −19,7% | −15,7% | +34,7% | −59,7% |
| 8 | −11,5% | −25% | +53,3% | −53,5% |
| 9 | +18,3% | −34,2% | −11,5% | −30,8% |
| 11 | −20% | −18,6% | −14,5% | −18,8% |
| 13 | −10,7% | −16,6% | −15,3% | −34,3% |
| 14 | −19,5% | +18,6% | +14% | −41,9% |

*The chemical structure of the compounds are shown in table B, page 11.

These products were also shown to have a reduced toxicity, for example the compounds 6 and 7 possess an oral LD$_{50}$ value in mice greater than 600 mg/kg.

This set of properties allows the compounds according to the invention to be recommended as cardiovascular-medicaments especially for the treatment of angina pectoris.

The compounds of the invention may be administered enterally or parenterally, preferably in a daily dose from 1 to 10 mg per kg bodyweight. The preferred doses in human beings may vary between 100 and 600 mg per day.

Mixed with suitable auxiliaries the compounds I may be compressed into solid dosage units such as pills, tablets, coated tablets or be processed into capsules. By means of suitable liquids the compounds may also be applied as an injection or oral preparation in the form of solutions, suspensions or emulsions.

By a lower alkyl group in the definition of $R_1$, $R_2$, $R_3$, $R_4$, $R_5$ and $R_6$ is to be understood an alkyl group with 1 to 6 carbon atoms, such as methyl, ethyl, propyl, isopropyl, butyl, isobutyl, tert.butyl, pentyl, hexyl.

The cycloalkyl radical in the definition of $R_1$ and $R_2$ is preferably a cyclohexyl or cycloheptyl radical.

By the heterocyclic amino radical as used in the definition of $R_4$ and $R_5$ is meant a 5- or 6-membered nitrogen containing ring which optionally may possess one additional hetero-atom, such as a pyrrolidinyl or morpholino radical. The pyrrolidinyl radical is the preferred radical.

With respect to the definition of $R_1$ and $R_2$ preference is given to the radicals methyl, phenyl or cyclohexyl.

The preferred $R_3$ radical is hydrogen, methyl or phenyl.

The radical which is most preferred in the definition of $R_6$ is the isobutyl radical.

Preferred compounds according to the invention are the compounds 1 and 6 of Table B.

The compounds of formula I possess a chiral carbon in case $R_1$ and $R_2$ are different radicals. In such case both the racemic mixture I as well as the separate optical enantiomers belong to the compounds of the invention. The said optical enantiomers can be prepared in the usual manner by resolution of the racemic mixture or directly using optically active starting products.

EXAMPLE 1

1-[1-(1-propynyl)-cyclohexyloxy]-2-(N-pyrrolidinyl)-3-iso-butoxypropane 33 g of 1-pyrrolidinyl-2-chloro-3-isobutoxypropane were gradually introduced into a reactor containing 41.4 g of 1-propynyl cyclohexanol, 30 g of sodium-hydroxide previously dissolved in 30 ml of water and 3.1 g of benzyl triethylammonium chloride, while stirring well. When the addition had ended, the mixture was refluxed for 4 hours while the stirring was maintained. After cooling, the product formed was extracted with ether. The ether phase was filtered, decanted and washed with water, dried over sodium sulphate and then evaporated. After distillation of the residue 22 g of the product of the heading were obtained in the form of a clear yellow liquid. BP$_{0,5}$=130°–135° C., n$_D^{20}$=1,483.

EXAMPLE 2

1-(1-methyl-1-phenyl-2-propynyloxy)-2-(N-pyrrolidinyl)-3-isobutoxy propane

In a corresponding manner as described in the previous example 6 g of the liquid product of the heading were obtained by refluxing for 5 hours a mixture constituted by 14.6 g of 2-phenyl-3-butyne-2-ol, 10 g of sodium hydroxide in 10 ml of water, 1,1 g of benzyl triethylammonium chloride and 11 g of 1-pyrrolidinyl-2-chloro-3-isobutoxy propane. BP$_{0,5}$=143°–145° C.; n$_D^{20}$=1.502.

The liquid base thus obtained was converted into the hydrochloride salt. Melting point HCl salt: 154° C. Elemental analysis:

| | C % | H % | N % |
|---|---|---|---|
| Theoretical | 68.92 | 8.81 | 3.83 |
| Found | 67.62 | 8.63 | 3.79 |

EXAMPLE 3

1-(1-methyl-1-phenyl-2-propynyloxy)-2-(N-pyrrolidinyl)-3-phenoxy propane 27.5 g of 1-pyrrolidinyl-2-chloro-3-phenoxy propane were gradually introduced into a reactor containing 29.2 g of 2-phenyl-3-butyne-2-ol, 20 g of sodium hydroxide in 20 ml of water and 2.27 g of benzyl triethylammonium, while stirring well. When the addition ended, the reaction medium was very thick and 20 ml of benzene were added before refluxing for 5 hours. The product was then extracted with ether, filtered, washed and dried as indicated in Example 1.

After distillation, 21 g of the product of the heading were collected having a boiling point: BP$_{0,5}$=190° C. and e refractive index n$_D^{20}$=1.550.

EXAMPLE 4

1-(1-methyl-1-phenyl-2-propynyloxy)-2-(N-pyrrolidinyl)-3-(1-ethynyl cyclohexyloxy)-propane Initially, the mesylate was prepared by adding, drop by drop, 23 ml of mesyl chloride to 56 g of 1-(1-ethynyl cyclohexyloxy)-3-(N-pyrrolidinyl) propane-2-ol in 135 ml of pyridine, the temperature of the reaction medium being kept between 0° C. and −5° C. When the reaction had ended, the mesylate formed was extracted with chloroform, and then with ether.

After purification and elimination of the ether, the starting product obtained was used in the following reactionstep.

16 g of mesylate of 1-(1-ethynyl cyclohexyloxy)-3-(N-pyrrolidinyl) propane-2-ol were added drop by drop at ambient temperature to a reactor containing 10 g of 2-phenyl-3-butyne-2-ol, 10 g of sodium hydroxide in 10 ml of water and 1.1 g of benzyl triethylammonium chloride. When the addition was finished, the reaction medium was fairly thick; refluxing was then carried out gently, while stirring moderately. Refluxing was maintained for about 14 hours and then, after cooling, the product of the heading was extracted with ether, as indicated in Example 1. After distillation, 24 g of product were collected having a refractive index $n_D^{20} = 1.523$.

EXAMPLE 5

Compounds whose characteristics are summarized in Table B hereinafter were also prepared in accordance with the process described in Example 4:

TABLE B

| Compound no. | R$_1$ | R$_2$ | R$_3$ | —NR$_4$R$_5$ | R$_6$ | F °C. (salt) or $n_D^{20}$ (base) |
|---|---|---|---|---|---|---|
| 1 see also (Example 2) |  | —CH$_3$ | H |  | —CH$_2$—CH(CH$_3$)$_2$ | F$_{HCl}$ = 154° C. |
| 2 |  | —CH$_3$ | H | —N(C$_2$H$_5$)$_2$ | 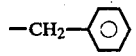 | $n_D^{20}$ = 1,526 |
| 3 see also (Example 3) |  | —CH$_3$ | H |  |  | $n_D^{20}$ = 1,550 |
| 4 |  | —CH$_3$ | H |  | —C$_2$H$_5$ | $n_D^{20}$ = 1,510 |
| 5 compound of (Example 4) |  | —CH$_3$ | H |  |  | $n_D^{20}$ = 1,523 |
| 6 see also (Example 1) |  | | —CH$_3$ |  | —CH$_2$—CH(CH$_3$)$_2$ | $n_D^{20}$ = 1,483 |
| 7 |  | | H |  | —CH$_2$—CH(CH$_3$)$_2$ | $n_D^{20}$ = 1,480 |
| 8 |  | | H |  | —(CH$_2$)$_3$—CH$_3$ | $n_D^{20}$ = 1,483 |
| 9 |  | | | 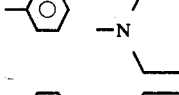 | —CH$_2$—CH(CH$_3$)$_2$ | $n_D^{20}$ = 1,524 |
| 10 |  | —CH$_3$ | | 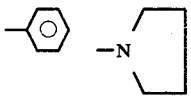 | —CH$_2$—CH(CH$_3$)$_2$ | $n_D^{20}$ = 1,525 |
| 11 | |  | H |  | —CH$_2$—CH(CH$_3$)$_2$ | $n_D^{20}$ = 1,481 |
| 12 | —C$_2$H$_5$ | —(CH$_2$)$_3$—CH$_3$ | | 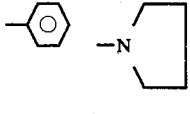 | —CH$_2$—CH(CH$_3$)$_2$ | $n_D^{20}$ = 1,493 |

TABLE B-continued

| Compound no. | R₁ | R₂ | R₃ | —NR₄R₅ | R₆ | F °C. (salt) or n_D²⁰ (base) |
|---|---|---|---|---|---|---|
| 13 | —CH₃ | —CH₂—CH(CH₃)₂ | H | pyrrolidinyl | —CH₂—CH(CH₃)₂ | n_D²⁰ = 1,459 |
| 14 | —CH₃ | —CH₃ | H | pyrrolidinyl | —CH₂—CH(CH₃)₂ | F_fumarate = 135° C. |

We claim:

1. A compound of the formula:

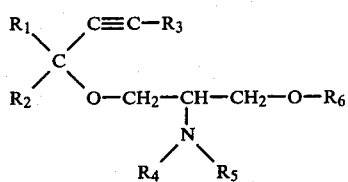

or a pharmaceutically acceptable salt thereof, in which $R_1$ and $R_2$ each represent, independently of one another, a $C_1$-$C_6$ alkyl radical or a phenyl radical, or, together with the carbon atom to which they are attached, form a cycloalkyl radical having at the most 7 carbon atoms; $R_3$ represents hydrogen, a $C_1$-$C_6$ alkyl radical or the phenyl radical; $R_4$ and $R_5$, together with the nitrogen atom to which they are attached, form a pyrrolidinyl or morphilino radical, and $R_6$ represents a $C_1$-$C_6$ alkyl radical, a phenyl radical, a benzyl radical, or the 1-ethynylcyclohexyl radical.

2. Compound according to claim 1, in which $R_1$ is methyl, $R_2$ is phenyl, $R_3$ is hydrogen, $R_6$ is isobutyl and the group $NR_4R_5$ is the pyrrolidinyl radical.

3. Compound according to claim 1, in which $R_1$ and $R_2$ together with the carbon atom to which they are bound represent the cyclohexyl radical, $R_3$ is methyl, $R_6$ is isobutyl and the group $NR_4R_5$ represents the pyrrolidinyl radical.

4. Compound according to claim 1, in which $R_1$ is phenyl, $R_2$ is methyl, $R_3$ is hydrogen, $R_6$ is ethyl and the group $NR_4R_5$ is the morpholino radical.

5. Pharmaceutical composition useful in the treatment of angina pictoris comprising an effective amount of at least one compound in accordance with any one of claims 1, 2, 3 or 4, in association with appropriate pharmaceutical excipients.

6. A method of treating patients with angina pectoris wherein a compound according to any one of claims 1, 2, 3 or 4 is administered to said patients at daily doses of between 100 and 600 mg.

* * * * *